United States Patent
Duchateau et al.

(10) Patent No.: US 6,312,711 B1
(45) Date of Patent: Nov. 6, 2001

(54) PHARMACEUTICAL OR FOOD COMPOSITION FOR TREATING PATHOLOGIES RELATED TO GRAFT VERSUS HOST, ALLERGIC OR AUTOIMMUNE REACTION

(75) Inventors: Jean Duchateau, Brussels; Genevieve Servais, Horrues, both of (BE)

(73) Assignee: Universite Libre de Bruxelles, Brussels (BE)

( * ) Notice: Subject to any disclaimer, the term of this patent is extended or adjusted under 35 U.S.C. 154(b) by 0 days.

(21) Appl. No.: 09/380,548

(22) PCT Filed: Mar. 5, 1998

(86) PCT No.: PCT/BE98/00030

§ 371 Date: Oct. 28, 1999

§ 102(e) Date: Oct. 28, 1999

(87) PCT Pub. No.: WO98/39029

PCT Pub. Date: Sep. 11, 1998

(30) Foreign Application Priority Data

Mar. 5, 1997 (BE) .................................................. 9700199

(51) Int. Cl.[7] .......................... A61K 39/00; A61K 39/38
(52) U.S. Cl. .................. 424/439; 424/184.1; 424/190.1; 424/434; 424/275.1; 424/535; 424/538; 424/193.1
(58) Field of Search ................................ 424/193.1, 439, 424/184.1, 190.1, 275.1, 535, 538, 434; 514/2; 530/403

(56) References Cited

U.S. PATENT DOCUMENTS 6,017,540 * 1/2000 Srivastava et al. ............... 424/193.1

FOREIGN PATENT DOCUMENTS

| 94/29459 | 12/1994 | (WO) . |
| 95/24923 | 9/1995 | (WO) . |
| WO96/13723 | 5/1996 | (WO) . |
| WO96/36880 | 11/1996 | (WO) . |
| 97/06821 | 2/1997 | (WO) . |
| 98/23735 | 6/1998 | (WO) . |

OTHER PUBLICATIONS

Barrios et al., "Mycobacterial heat–shock proteins as carrier molecules . . . ", *European Journal of Immunology*, 1992, vol. 22, p. 1365–1372.

Michilis et al., "Fine Tuning of Epitopic Dominance Induced by Lung Cancer on the IgG Response to Bovine Batalactoglobulin," *Cancer*, 15.02.96, vol. 77, No. 4, p. 657–664.

Strobel et al., "Immune responses to dietary antigens: oral tolerance," *Immunology Today*, Apr. 1998, vol. 19, No. 4, p. 173–181.

McGhee et al., "Mucosal Immune Responses: An Overview," *Mucosal Immunology*, 1999, p. 485–506.

Pharmacia & Upjohn, *Pharmacia Cap System Allergens*.

Hendrick et al., "Molecular Chaperone Functions of Heat–Shock Proteins," *Annual Review of Biochemistry*, 1993, vol. 62, p. 349–383.

Roitt, *Essential Immunology*, 1988, Blackwell Scientific Publications, Oxford.

Polla et al., "Presence of hsp65 in bacterial extracts (OM–89): a possible mediator of orally–induced tolerance?".

(List continued on next page.)

*Primary Examiner*—Thurman K. Page
*Assistant Examiner*—Liliana Di Nola-Baron
(74) *Attorney, Agent, or Firm*—Merchant & Gould P.C.

(57) ABSTRACT

The invention concerns a pharmaceutical and/or food composition comprising a suitable pharmaceutical and/or food vehicle and a heat shock protein and at least conformation or sequential epitopes of an antigenic structure inducing a graft versus host, an allergic or autoimmune reaction.

19 Claims, 4 Drawing Sheets

OTHER PUBLICATIONS

XP-002083262; Self and Foreign 60—Kilodalton Heat Shock Protein T Cell Epitope Peptides Serve As Immunogenic Carriers for a T Cell—Independent Sugar Antigen; Stephanie Konen–Waisman, Mati Fridkin, and Irun R. Cohen; Department of Organic Chemistry and Department of Cell Biology, The Weizmann Institute of Science, Rehovot, Israel; pp. 5977–5985; Mar. 10, 1995.

* cited by examiner

PHARMACEUTICAL OR FOOD COMPOSITION FOR TREATING PATHOLOGIES RELATED TO GRAFT VERSUS HOST, ALLERGIC OR AUTOIMMUNE REACTION

SUBJECT OF THE INVENTION

The present invention relates to a novel pharmaceutical or food composition intended for treating pathologies associated with graft rejection or an allergic or autoimmune reaction.

TECHNOLOGICAL BACKGROUND OF THE INVENTION

In the last twelve years, controlled studies have described desensitization based on the oral administration of allergens (1). This method is based on the fact that the oral administration of an antigen facilitates the acquisition of an immunological tolerance to it. The digestive route constitutes the mode of contact of the body with antigens, of food or microbial origin. However, allergic reactions are rare. Oral administration of sheep red blood cells (SRBC) to rats prevents the rats from later producing anti-SRBC antibodies after a subcutaneous injection, whereas, without the prior oral intake, the allergic response would have been present. This phenomenon constitutes what is referred to immunologically as oral tolerance.

This oral desensitization method has been validated in prospective and controlled studies, and makes it possible to reduce the risks of anaphylaxis, in particular for birch pollen and acari. It is already available on the vaccines market in a presentation in drinkable form (sold by the company Laboratoire des Stallergènes—Paris).

Moreover, it may be considered that the benefit, in terms of protecting infants against allergy to milk, which has been observed since the introduction of new, enzymatically pre-digested powdered milk formulations, would result from the induction of immunological tolerances by the presentation of antigens in the form of peptides.

However, it is difficult to predict or state the efficacy of the desensitization. Clinical observation makes it possible, after the event, to confirm or deny any improvement in the symptoms.

It is known, from international patent application WO 96/36880, to be able to detect and/or quantify ligands specific to a pathology associated with an allergic or autoimmune response or lung cancer, by means of a test of competition between ligands present in a sample and other discriminable ligands. This test is based on the fact that allergic and symptomatic individuals recognize, by means of their antibodies, epitopes different from those recognized by the antibodies of tolerant individuals on the same specific antigenic structure of said pathology. That document also describes the possibility of measuring the evolution of this specificity, in particular in the case of children who are allergic to milk and the change toward the in vivo acquisition of tolerance to milk.

AIMS OF THE INVENTION

The aim of the present invention is to provide a novel composition, which may be of pharmaceutical or food type, designed to modify the immune response of patients toward a pathology associated with an allergic or autoimmune reaction or toward graft rejection phenomena, such that the immune response of said patients comes close to the natural tolerance manifested by normal individuals (who remain free of symptoms although they are also liable to be exposed to this pathology).

The present invention is also directed toward providing an inexpensive pharmaceutical or food composition which is easy to administer and which can be used in a prophylactic and/or therapeutic manner.

CHARACTERISTIC ELEMENTS OF THE INVENTION

The present invention relates to a pharmaceutical or food composition comprising an adequate pharmaceutical or food vehicle, a stress protein (also known as "heat shock protein" or HSP) and at least one of the epitopes (conformational or sequential epitope) of an antigenic structure, said antigenic structure inducing graft rejection, an allergic reaction or an autoimmune reaction. Preferably, the pharmaceutical or food vehicle of the composition is adequate for mucosal (in particular oral) or cutaneous administration.

Advantageously, the stress protein and the epitope form a complex naturally (i.e. without formation of a covalent bond), as described by Roamn et al., Febs (1994), Fouri et al., The Journal of Biological Chemistry, Volume 269 No. 48, pp. 30470–30478 (1994), Palleros et al., The Journal of Biological Chemistry, Volume 269 No. 48, pp. 13107–13114 (1994), Grageroov and Gottesman, Journal of Molecular Biology, No. 241, pp. 133–135 (1994), and Schmid et al., Science, Volume 260, p. 1991 (1994) incorporated below by way of reference.

According to the invention, the epitope (also known as the antigenic determinant) is obtained by a hydrolysis, preferably an enzymatic hydrolysis, in particular with pepsin, of said antigenic structure.

Advantageously, the stress protein is a bacterial stress protein present, for example, in saprophytic bacteria such as *E. coli*.

Among the stress proteins of the present invention, mention may be made of the stress protein GroEL, the stress proteins GrpE, DnaK or DnaJ as described in particular by Hendrick and Hartl (Annual Review of Biochemistry, No. 62, p. 349 (1993)) or the heat shock proteins HSP 60, 70, etc.

The expression "phenomenon of graft rejection or allergic or autoimmune reaction" means hypersensitivity reactions of immediate or delayed type brought about by contact in particular with an allergen (this reaction can be immediate and specific (anaphylaxis, urticaria, etc.) or delayed over time) or autoimmune diseases and disorders of the immune system of immediate or delayed type associated with graft rejections of host against graft type and graft against host type.

Autoimmunity is a state of immunization of an individual against his or her own constituents, and the phenomenon of graft rejection is a state of immunization of an individual against foreign constituents (bodily fluids such as blood, cerebrospinal fluid, etc., cells, tissues, organs, antibodies, etc.) deliberately implanted into the patient. These phenomena are observed in particular in pathologies chosen from the group consisting of infections associated with SLE (Systemic Lupus Erythematosus disease), Gougerot-Sjögren syndrome (or Sjögren's disease) and rheumatoid polyarthritis, as well as pathologies such as sarcoidosis and osteopenia, spondylarthritis, scleroderma, multiple sclerosis, amyotrophic lateral sclerosis, hyperthyroidism, Addison's disease, autoimmune hemolytic anemia, Crohn's disease, Goddpasture's syndrome, Graves' disease, Hashimoto's thyroiditis, idiopathic purpural hemorrhage, insulin-dependent diabetes, myasthenia, pemphigus vulgaris, pernicious anemia, poststreptococcal glomerulonephritis, psoriasis and spontaneous sterility, as well as immediate or delayed phenomena observed during graft rejections.

The expression "antigenic structure which induces graft rejection or an allergic or autoimmune reaction" means allergens, preferably chosen from the group consisting of the major allergic antigens present in foods such as eggs, soya and milk, in particular bovine beta-lactoglobulin (BLG) from cow's milk, the major allergic antigens present in plants, molds, medicines (in particular antibiotics) and pollens, the major allergic antigens present in animals, in particular in hairs, and venom, in particular wasp venom, the major antigens of the allergic reaction to acari, to the mite present in house dust (antigen P1 *Dermatophagoides pteronyssinus*), the major antigen of *Aspergillus fumagatus*, and staphylococcal enterotoxin B (SEB).

Other non-limiting examples of allergens or mixtures of allergens have also been described in the publication ISBN-91-970475-5-4 by Pharmacia AB, which is incorporated herein by way of reference.

The "antigenic structure" can also be an antigenic complex which induces an autoimmune disease. Preferably, this antigenic structure is specific to lupus (SLE) or Sjögren's disease, in particular the plasma membrane or a portion of this membrane containing membrane DNA with a weight of greater than 100 KD, in particular as described in patent application WO 96/13723, the publication number of 20 which is incorporated by way of reference.

Other non-limiting examples of antigenic complexes which induce autoimmune diseases have also been described by Roitt I. M. (Essential Immunology, Blackwell Scientific Publication (ch. 14) ISBN 0-632-01994-8) and by Humbel R. L. (Auto-anticorps et maladies auto-immunes [Autoantibodies and autoimmune diseases], Ed. Scientifiques Elsevier (1994) ISBN 2-906077-58-5).

This antigenic structure can also be a major histocompatibility locus (MHC I and/or MHC II) or a portion thereof which is specific to an individual and is involved in graft rejection phenomena (including bodily fluid transfusions).

The appropriate pharmaceutical or food vehicle according to the present invention may be any additive or support, such as a nontoxic compatible substance for administration of the composition according to the invention to a patient. The type of appropriate pharmaceutical or food vehicle used will depend on the mode of administration, selected. In particular, for oral administration, these vehicles can consist of aqueous solutions, syrups, lozenges, capsules, etc. Other pharmaceutical vehicles such as creams or ointments may be chosen depending on the type of administration, in particular for cutaneous administrations.

A person skilled in the art can also adapt the pharmaceutical vehicle as a function of a subcutaneous, intradermal, intravenous, intramuscular or parenteral administration, via nasal or oral inhalation, etc.

The percentage of active compound present in the composition according to the invention will depend on the type of patient, the pathology treated and the route of administration. The doses will be limited only by the patient's tolerance to the product, as well as by the administration rates.

The administration concentrations will be chosen in particular such that the abovementioned pathological signs and symptoms are reduced, preferably eliminated, by the administration doses envisaged by the posology.

The inventors have discovered, unexpectedly, that the use of the pharmaceutical and/or food composition according to the invention makes it possible to modify the immune response of a patient induced with said antigenic structure. The modification of a patient's immune response can be detected and quantified in particular according to the process and technique described in patent application WO 96/36880 or by any method of clinical analysis of the treated patient (including prophylactic methods) which is well known to those skilled in the art.

Another aspect of the present invention relates to the use of the composition according to the invention for the preparation of a medicine designed to modify a patient's immune response toward an antigenic structure which induces graft rejection or an allergic or autoimmune reaction. In particular, the present invention relates to the use of the pharmaceutical and/or food composition according to the invention for the preparation of a medicine intended to desensitize atopic or non-atopic allergies.

Another aspect of the present invention relates to the use of the pharmaceutical and/or food composition according to the invention for the preparation of a medicine intended for the prevention or treatment of the abovementioned allergic reactions and autoimmune diseases, for the treatment or prevention of graft rejections, optionally in combination with a specific product for reducing or neutralizing allergic reactions, autoimmune reactions and graft rejection phenomena (in particular the administration of immunosuppressants such as azathioprine, steroids, antilymphocyte globulins, cyclosporin A, rapamycin, KF-506 (tacrolimus) or lymphokines (in particular IL-10), and the analogs and agonists thereof which are well known to those skilled in the art.

The terms "analogs" and "agonists" of these molecules means other molecules, or derivatives of these molecules, which act on the same receptor or via the same mechanism of action as the abovementioned specific products.

The present invention also relates to a process for the therapeutic or prophylactic treatment of a patient, comprising the step of administration of the composition according to the invention to said patient so as to modify the patient's immune response toward an antigenic structure which induces graft rejection or an allergic or autoimmune reaction.

Figure 1:
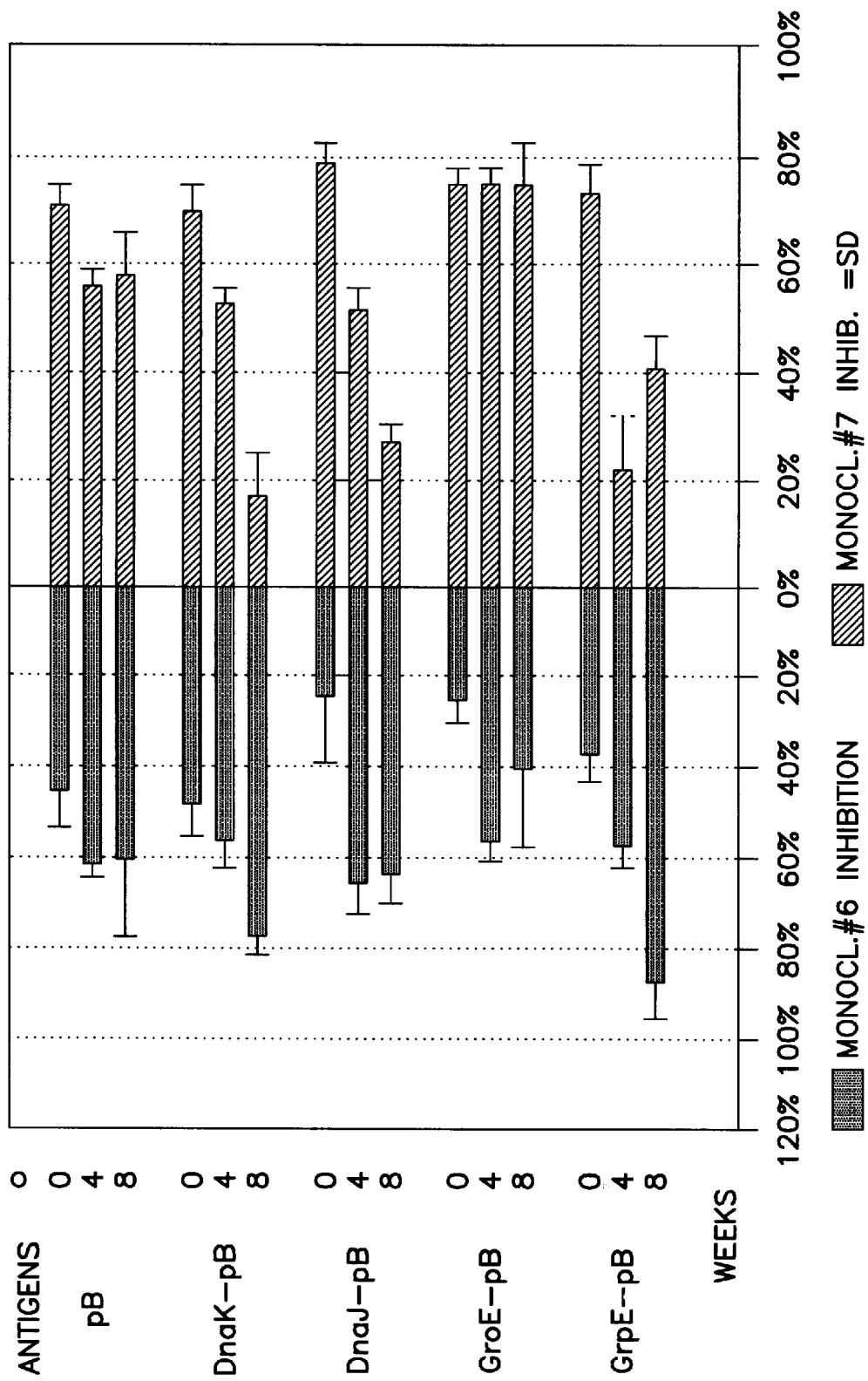
FIG. 1 depicts a change in average inhibition (+standard deviation) of the binding of M6 (left hand side of FIG. 1) and M7 (right hand side of FIG. 1) monoclonal antibody by the individual sera, for the various treatment groups.

The present invention will be described in greater detail with reference to the figures described in the implementation examples below.

EXAMPLES

A. Basis of the Model Considered a) Using the Oral Route

Oral administration allows an induction of immunological tolerances, and is increasingly widely applied in the field of antiallergic desensitization. However, it requires the use of larger amounts of antigens than via the parenteral route, and has to extend over periods of at least several years (2, 3). Optimization of the dose administration regime and of their periodicity can be adapted by a person skilled in the art so as to avoid syndromic reactions (replication of the allergic symptomatology in the case of an overdose), which are frequent but not dangerous on account of the slow progression in the increase of the doses administered (2).

b) Using Peptide-Stress Protein Complexes

Stress proteins (heat shock proteins (HSP)) constitute a series of protein families, which have been highly conserved during evolution from bacteria through to man, and which have the capacity to bind to peptides or to proteins whose conformational structure is altered or on course to its final conformation (4).

They have several roles, including participation in intracellular transport leading to polypeptide assembly for the synthesis of certain proteins or their elimination. Some are expressed at the surface of different cells and can contribute to the antigenic presentation, in particular to T lymphocytes to the receptors for antigen of gamma-delta type, which colonize the mucous membranes and lymphoid organs associated with the digestive mucosa.

The antigenic presentation via HSPs of the family HSP70, to gamma-delta ($\gamma$, $\delta$) T lymphocytes makes it possible to dispense with the presentation dependent on the type II major histocompatibility complex.

Parenteral injection of HSP-peptide complexes into experimental animals makes it possible to obtain a noteworthy adjuvant effect (5, 6) which determines or amplifies the antigenic power of these peptides.

Certain bacterial HSPs of the families HSP60 and HSP70 are the target of immune responses which have a protective role with regard to infection with these microorganisms.

It has recently been proposed to perform desensitization orally by giving peptide extracts of *E. coli* containing HSP60 to patients suffering from rheumatoid arthritis, with a certain beneficial effect (5, 6). Considering the negligible side effects, the authors propose to attempt the test on other inflammatory complaints in order to manipulate a response directed against one of these microbial HSPs itself, which is considered as an auto-antigen substitute.

The inventors have discovered, unexpectedly, that stress proteins constitute a noteworthy vector for presenting peptides to lymphoid systems of the digestive tract and inducing a tolerance. The stress proteins of saprophytic bacteria appear to be the ones which are the most abundant in nature in the digestive lumen. It is also probable that the peptides derived from the digestion of food constitute the most abundant mass of antigenic fragments available for the formation of HSP-peptide complexes. However, the abundance of the peptides generated, and the presumed limited amount of bacterial HSPs makes the formation of an immunologically efficient amount of these HSP-antigenic peptide complexes uncertain, and all the more so since the absorbed amount of antigen with desensitizing intent is very low (a few tens of $\mu$g) with regard to the food protein load.

The inventors have proposed to promote the formation of these complexes before arrival in the digestive tract, i.e. in vitro, by using purified *E. coli* stress proteins and peptides derived from the digestion of BLG with pepsin.

c) Using Tests of Competition Between Serum Antibodies and Monoclonal Antibodies for BLG The two monoclonal antibodies referred to below as M6 and M7 each recognize a different conformational epitope on the BLG molecule. Their different qualitative properties are used as recognition markers for single epitopes in a competition with all of an individual's serum antibodies. It emerges from clinical studies that symptomatic individuals and asymptomatic individuals recognize on this molecule epitopes which, for at least a part, are different (7), which are referred to below as epitopic profiles.

The epitope recognized by M6 is recognized particularly well by allergic and symptomatic individuals. Binding of the M6 antibody to intact BLG is actually better inhibited by the sera of children who are allergic to milk than by the sera of non-allergic individuals, whether these are children or adults in good health (blood donors).

The epitope recognized by M7 is better recognized by asymptomatic individuals than by allergic individuals. Binding of the M7 antibody to BLG is better inhibited by asymptomatic individuals than by allergic individuals.

Antigenic binding competitively against M6 is used as a specificity index representing the epitopic profile recognized by the allergic individuals, and in a complementary manner, the competition against M7 as a specificity index representing the epitopic profile recognized by the asymptomatic individuals.

Validation of this interpretation was confirmed longitudinally by clinical studies. The acquisition of a state of tolerance to milk is accompanied by a conversion of the fine specificity of the serum antibodies, toward the standard profile of asymptomatic individuals.

It is this epitopic discrimination expressed at the level of the circulating antibodies which serves here as an analytical tool for influencing oral antigenic modulation.

B. Experimental Model

Syngenic mice received, in their drinking water, very small amounts of peptides derived from the peptic digestion of beta-lactoglobulin (BLG), which were precoupled or otherwise with purified stress proteins and whose functional capacity was intact (capacity to bind to impaired peptides or proteins).

a) Animal Origin and Rearing Conditions 40 individuals 8 to 16 weeks old were taken from a rearing stock of Balbc mice fed for several generations on a diet poor in cow's milk: 13 $\mu$g of beta-lactoglobulin/gram of nutrient granules.

b) Preparation of the Antigenic Complexes

BLG was digested on contact with pepsin coupled to agarose (Sigma) under incomplete digestion conditions, and then filtered on a 10,000 dalton filter. The concentration of the digestion product (pB) was measured by spectrophotometry (yield of 30 to 50% of intact protein).

1 μg/ml phosphate buffer solutions (PBS) were incubated with 1 μg/ml solutions of the following E. coli stress proteins: DnaK, DnaJ, GroEL, GrpE (Stressgen) for at least one hour at ambient temperature. 1 ml aliquots of each combination were frozen.

c) Treatment Groups and Oral Posology of the Complexes

A solution of complexes (1 ml) was added, after thawing, to the 100 ml water bottle given daily to each cage of four mice. Each type of complex is administered to 8 mice. A control group receives the non-complexed pB antigen.

The solution was added 3 times a week for two weeks (i.e. six times), from time zero.

d) Antibody Response

An individual sample of blood was taken from the retro-orbital plexus at time zero and after 4 weeks. The animals are anaesthetized with ether and then exsanguinated, after 8 weeks.

The specificity of the serum antibodies was examined by an ELISA type competitive test.

e) Test of Antibody Specificity by Competition

Polystyrene multiwell plates are passively covered, by absorption at ambient temperature, with a small amount of BLG (0.3 μg/ml in bicarbonate buffer) and then saturated with gelatin (1%, weight/vol—Haemacel (R)).

The mouse serum is diluted 100-fold with dilution buffer (PBSdil) consisting of: PBS-EDTA (10 mM)—Tween 20 (0.05%)—gelatin (Haemacel—1%).

Two murine monoclonal antibodies produced were selected for their specificity with regard to conformational epitopes of BLG. They were biotinylated and are used at their limit dilution for antigenic binding, defined in the following way: the dilution which allows a maximum signal but which is sensitive to any reduction in the antigen load, at its specific dilution, and which can be competitively inhibited with a pool of sera from untreated mice. The reason for this is that the latter produce natural antibodies against BLG, in relation to exposure to the food antigen, even minimal exposure.

100 μl of diluted serum and of biotinylated antibody are mixed together in a well, in duplicate.

After incubation overnight at ambient temperature, the binding of the monoclonal antibody is measured by the proportional retention of biotin revealed by uptake of streptavidin coupled to horseradish peroxidase. This peroxidase colors an ortho-phenylenediamine substrate. The optical density (O.D.) is measured by spectrophotometry. The background noise (b.n.) is measured in antigen-free wells. The maximum binding is defined either in the absence of competition (monoclonal antibody alone) or in the presence of relatively non-inhibiting serum.

The results are expressed as a percentage of inhibition of binding of the monoclonal antibody by: % inhibition=100× (test O.D.–b.n. O.D.)/(maximum O.D.–b.n. O.D.)

The correspondence between the profile of epitopes recognized on the antigen and the individual's clinical state (tolerance or otherwise) is confirmed by other examples: model of allergy to acari:
   the evolution of the fine specificity of anti-acari antibodies in allergic children shows the existence of an epitopic profile under the effect of the desensitization induced both parenterally and orally,
the evolution of the antibodies

DESCRIPTION OF THE DRAWINGS g) Results

FIG. 1 summarizes the experimental data:
Inhibition of the M6 Antibody

The left-hand side shows the changes in the averages of inhibition (+standard deviation) of the binding of the M6 monoclonal antibody by the individual sera, for the various treatment groups.

The numerical data are compiled in Table 1.

The control group receiving the peptides digested with pepsin (pB) shows an increase in its average inhibition capacity from 45 to 60% and 59% after 4 and 8 weeks. This variation is significant ($p<0.05$—paired T test) relative to the start, but stable after 4 weeks.

For the group receiving the DnaK-pB complexes, this capacity rises from 48 to 56% and then 77% over the same period, the latter being greater than in the control group ($p<0.01$—non-paired T test) and very significant relative to the time zero ($p<0.001$—paired T).

Similarly, the groups receiving the complexes DnaJ-pB, GroEL-pB and GrpE-pB show a very significant increase after 4 weeks and which rises further at the eighth week (this value is considerably higher than the value of the control group for the complexes GroEL-pB and GrpE-pB at the corresponding moment).

Inhibition of the M7 Antibody

The right-hand side of FIG. 1 shows the changes in the averages of inhibition (+standard deviation) of the binding of the M7 monoclonal antibody, by the individual sera, for the various groups treated.

The numerical data are compiled in Table 2.

The control group receiving the BLG peptides digested with pepsin (pB) have an average inhibition capacity which falls from 70 to 52% and 57% in 4 and 8 weeks. This variation is significant ($p<0.01$—paired T test), although stable after 4 weeks.

For the group receiving the DnaK-pB complexes, this capacity already reduces significantly at the fourth week, falling from 68 to 51%, as in the control group.

However, the result collapses at 17% at the eighth week ($p<0.001$—paired T), which is markedly lower than that of the control group for the corresponding sample ($p<0.01$—non-paired T test).

The change is parallel to that for the group treated with the DnaJ-pB complexes.

For the group receiving GroEL-pB complexes, the reduction in the inhibitory power is immediately maximal, reaching 28% from the fourth week, and remains at the same level, 30%, at the eighth week.

In the group receiving GrpE-pB complexes the reduction in the inhibitory power is also immediately maximal, falling from 72 to 22% from the fourth week, but appears subsequently to diminish, returning to an average level of 41%.

h) Conclusion

The administration of peptides derived from the enzymatic digestion of a major milk antigen, in this instance beta-lactoglobulin, in the form of complexes associated with stress proteins according to the invention, and via the oral route, results in a radical and very rapid modification in the profile of the epitopes recognized by the circulating antibodies. These antibodies are naturally present in all the individuals exposed to the antigen via their food. In a model of mice, chronically exposed to a small amount of the antigen via this route, the dose of antigen administered over a brief period of time is very low, far below the amount ingested naturally (estimated at 0.25 μg per individual and per day of treatment in the form of complexes and 150 μg per individual and per day in the common diet).

The speed of the change is all the more noteworthy since the half-life of the serum antibodies, mainly IgGs, is 3 weeks, which means that at the eighth week, there should still be a quarter of the antibodies present at the end of the treatment of only 2 weeks. All the stress proteins used were efficient. In a second experiment with DnaK-pB complexes, an attempt to determine a lower limit dose was unsuccessful, despite the use of doses as much as 10 times lower (0.1 µg/100 ml bottle/3 days per week).

C. Orally Induced Tolerance with Regard to Major Histocompatibility Antigens

1. Experimental Model

Syngenic animals (Balbc mice) receive a protein preparation dissolved in their drinking water. It contains fragments of histocompatibility antigens from syngenic mice of another strain, any graft from which they would reject (C3H mice).

The tolerance-generating effect is expected to be enhanced when these fragments are combined with a bacterial stress protein (in this case Dnak from E. coli).

As a control, a group of mice receive, in the same manner, a complex of Dnak with peptide fragments similarly obtained from beta-lactoglobulin (major antigen of milk).

It should be expected that the oral sensitization would specifically attenuate the lymphocyte reactivity with regard to a strain of foreign lymphocytes of the same type as those used for the oral preparation and not with respect to an unrelated third strain.

2. Materials and Method a) Animals:

3 groups of 12 mice are taken from a rearing stock of syngenic mice of Balbc strain are reared in cages of 6 animals. Each group receives, for 2 weeks, one of the following preparations in the bottle of drinking water at a rate of 3 distributions per week (every other day and not at the weekend) and a dose of 1 µg of complex per 100 ml of water:

a complex of Dnak-beta-lactoglobulin peptides (control preparation)

a solution of pepsin-digested spleen lymphocyte membrane peptides (containing fragments of histocompatibility antigens) from CH3 mice a complex of these peptides associated with purified Dnak from E. coli (Stressgen).

b) Test of Acquired Tolerance (in vitro)

This test is based on a monodirectional mixed lymphocyte culture.

The responding cells are isolated from the spleen of the test animals. The lympho-monocyte cells are obtained after centrifugation on a density gradient with a ficoll-isopaque mixture (Pharmacia). They are resuspended using 4 million cells/ml in RPMI 1640 culture medium buffered with Hepes and with bicarbonate, supplemented with 2-mercaptoethanol, glutamine, geomycin and 10% calf serum.

The stimulating cells are obtained in the same way from mice of different strains, from their MHC: the C3H strain is a domestic (DOM) strain.

They are incubated for one hour in the presence of mitomycin in order to block their ability to multiply. They are then resuspended under the same conditions as the responding cells.

Lymphocyte Culture:

An equal volume of suspension (0.1 ml) of responding cells and of stimulating cells are mixed, in triplicate, in round-bottomed wells of polystyrene multiwell culture plates in order to be subsequently incubated in an air/$CO_2$ (95/5%; vol/vol), humidified incubator at 37.5° C. for 5 days.

Each microculture well receives 2 µc of 2 C/mM tritiated thymidine (Amersham) 16 hours before stopping the culturing, which is carried out using a MASH II machine which filters each microculture on a glass-fiber membrane which retains the cell nuclei.

The nuclear radioactivity of each pellet, which reflects the de novo incorporation of thymidine into DNA, is measured by liquid scintillation counting (Packard Tricarb).

The results are expressed in counts per minute and represent the average of 3 samples of the same culture at the individual scale.

c) Experimental Procedure

The samples are taken at 2 different times:

during the 3rd week following the start of the oral administration of one of the preparations, during the 7th week.

The animals are sacrificed 3 times per period.

Each culture experiment comprises 2 animals per group treated.

The mixed lymphocyte culture is prepared in parallel:

a) with respect to mitomycin-treated cells of C3H origin b) with respect to mitomycin-treated cells of DOM origin d) Preparation of the Peptides Lymphocytes (20 million) of a suitable mouse strain are isolated from the spleen. This is a mixture of T and B lymphocyte in approximately equal amounts and thus bearing antigens of type I and II. They are treated with ultrasound (3×10 sec) and then centrifuged at 1000×g for 10 minutes. The supernatant is collected and recentrifuged in the same way. Next, the supernatant is centrifuged twice at 8000×g. The final supernatant is enriched in cell membranes and freed of cell nuclear debris and Golgi apparatus. It is then subjected to digestion with pepsin coupled to agarose beads, at pH 2 in glycine buffer, for 1 h 30 min at 37° C. After gentle centrifugation to separate the agarose beads, and neutralization at pH 7 with TRIS buffer, the mixture is filtered through a filter (Millipore, limit 10 kD). The yield is about 500 µg of peptide (determination by spectrophotometry) referred to as LMp.

A solution of 50 µg of peptide is mixed with a solution of 50 µg of Dnak (Stressgen) to form a Dnak-LMp complex.

The Dnak complex with beta-lactoglobulin peptide (Bp) is made in the same way using peptides derived from the peptic digestion of purified beta- lactoglobulin (cf. above).

3. Results

Figure 2:
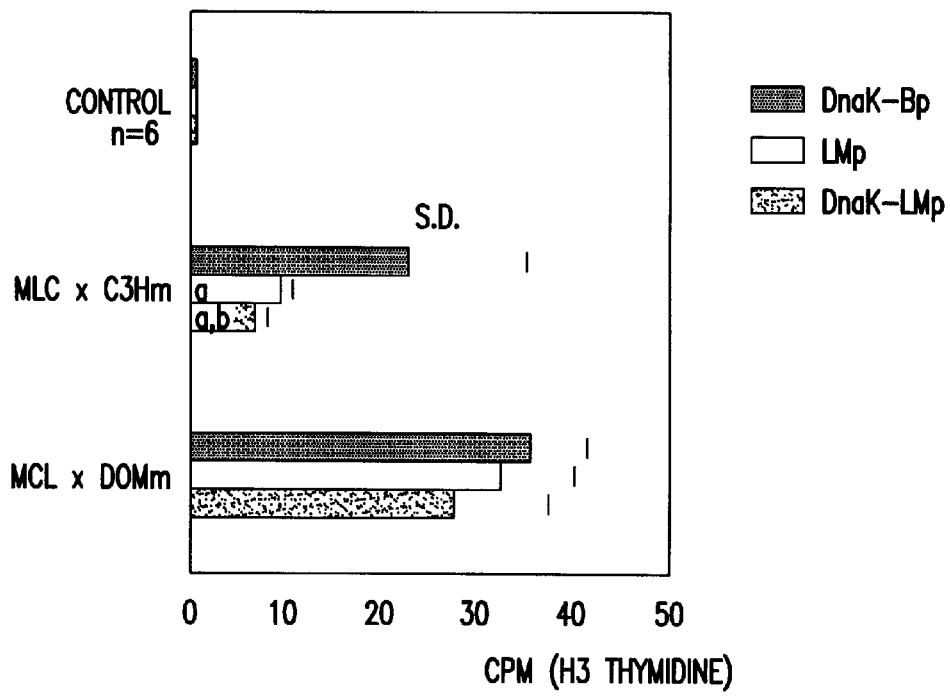
FIG. 2 depicts lymphocyte reactivity of three different groups of mice (one stimulated with mitomycin-treated cells of C3H origin, one treated with mitomycin-treated cells of a domestic strain, and a control) receiving a complex of Dna-K-beta-lactogloublin (DnaK-Bp), a solution of pepsin-digested spleen lymphocyte membrane peptides (LMp), and a complex of the LMp and purified Dna-K from *E. Coli* (DnaK-LNp) after 3 weeks.

After Treatment for 3 Weeks (FIG. 2)

The group of mice which received the Dnak-LMp complex responds the worst to the stimulation of mitomycin-treated C3H cells (C3Hm).

This is different ($p<0.02$; T-test) from the group which received the peptide LMp alone, and equal to that which received the Dnak-Bp control complex ($p<0.01$; T-test).

It should be noted, however, that administration of the peptide alone (without Dnak) also has an effect, since this group responds significantly less well than the control group ($p<0.01$; T-test).

However, the specificity of the response inhibition is guaranteed by the fact that the lymphocyte reactivity of the three groups is equivalent with regard to mitomycin-treated cells of a third, unrelated strain (DOMm).

Figure 3:
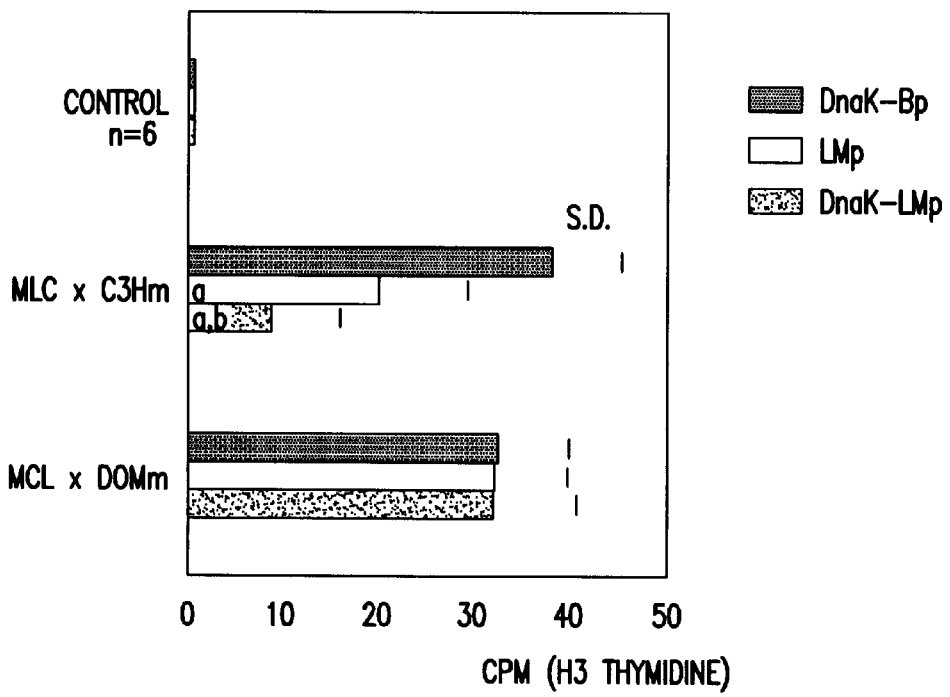
FIG. 3 depicts lymphocyte reactivity of three different groups of mice (one stimulated with mitomycin-treated cells of C3H origin, one treated with mitomycin-treated cells of a domestic strain, and a control) receiving a complex of Dna-K-beta-lactogloublin (DnaK-Bp), a solution of pepsin-digested spleen lymphocyte membrane peptides (LMp), and a complex of the LMp and purified Dna-K from *E. Coli* (DnaK-LNp) after 7 weeks.

After 7 Weeks (FIG. 3), or 4 Weeks After Stopping the Oral Administration

The differences between the 3 groups remain quite pronounced. The group treated with Dnak-LMp is the most inhibited with regard both to the group which received the membrane peptide alone ($p<0.02$; T-test) and to the control group ($p<0.01$; T-test).

Administration of the peptide alone again allows an attenuation of response with respect to the control group ($p<0.01$; T-test).

The specificity of the response is once again verified by the parallel test with respect to mitomycin-treated cells of an unrelated strain (DOMm) and in which the 3 differently treated groups react in the same way.

The administration of peptides obtained by peptic digestion of spleen lymphocytes from mouse strains characterized by an incompatibility in the H-2 system both at the K and D levels and the A–E levels in extremely low amounts and for two weeks, has the effect of strongly attenuating the unconditional response of immunocompetent lymphocytes, in vitro, which usually indicates this incompatibility.

This attenuation is enhanced by the presentation of this type of peptide in the form of peptide-Dnak complexes.

This attenuation is specific and in no way reaches the capacity of response with regard to a different variety, which bears no relation to the strain used for the tolerization.

D. Tolerance of Syngenic Mice with Regard to a Graft of Allogenic Cells

1. Model and Experimental Scheme

Mouse Strains:

Balbc for the animals made tolerant

C3H for the animals donating cells to be grafted (allogenic) and stimulating cells in mixed lymphocyte culture (MLC).

They are reared in cages of 6 animals. Each group consists of 12 animals per treatment.

The oral treatment is carried out according to the previous procedure.

Experimental Scheme:

Complexes administered in the drinking water:

Days 0, 2, 4, 7, 9

Allogenic graft: $20 \times 10^6$ intraperitoneal C3H spleen cells: Day 16

Sacrifice, collection of spleens and culturing of the spleen cells:

15 weeks after the graft

Detection and Counting of the Allogenic Cells a) By the Presence of Cells Bearing MHC Type II Functional test in bidirectional syngenic mixed culture.

The spleen cells of treated and grafted mice are cultured with cells from untreated (naive) syngenic mice (Balbc).

Normally, there is no proliferative response to be expected if the content of the spleen cells of treated and grafted animals is composed solely of syngenic cells.

On the other hand, the presence of allogenic cells, signaling the in vivo taking of the graft, should result in a proliferation of MLC type by the so-called naive, intolerant cells, which is proportionately greater the larger the number of foreign cells.

In order to evaluate the order of magnitude of the taking of the graft, an attempt at relative quantification of the response is carried out with reference to a dose/response curve obtained by adding known and increasing amounts of C3H allogenic cells to an identical amount of naive and responding cells ($200 \times 10^3$ cells/well).

b) By the Presence of Cells Bearing MHC Type I

Direct counting by flow cytofluorometry immunofluorescence using a mouse monoclonal antibody specific for MHC type I of the C3H mouse: H-2 kk (Serotec), coupled to fluorescein or to phycoerythrin on a suspension of spleen cells.

2. Results

Figure 4:
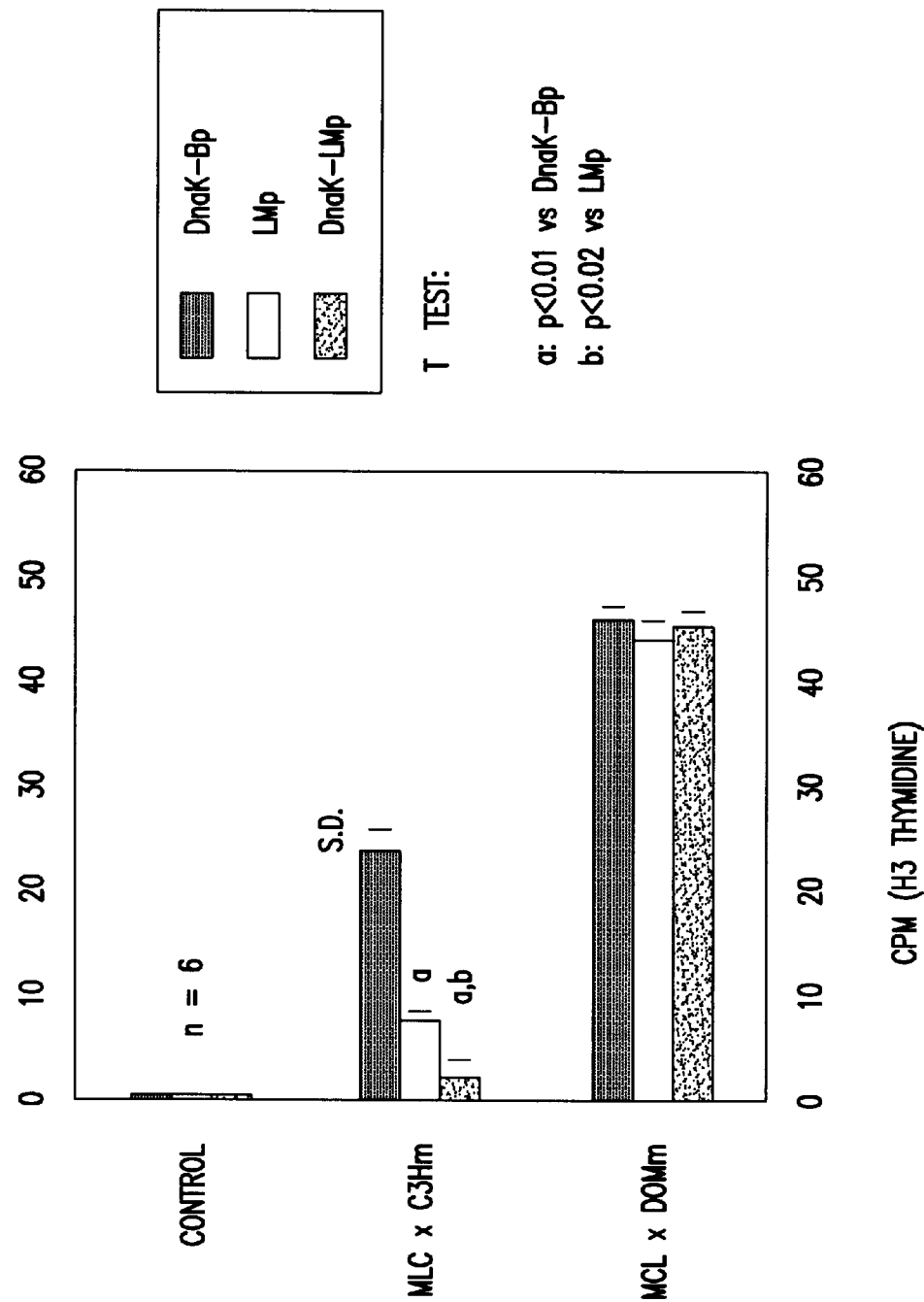
FIG. 4 depicts lymphocyte reactivity of three different groups of mice (one stimulated with mitomycin-treated cells of C3H origin, one treated with mitomycin-treated cells of a domestic strain, and a control) receiving a complex of Dna-K-beta-lactogloublin (DnaK-Bp), a solution of pepsin-digested spleen lymphocyte membrane peptides (LMp), and a complex of the LMp and purified Dna-K from *E. Coli* (DnaK-LNp) after 15 weeks.

As seen in FIG. 4, 15 weeks after the peritoneal graft, the spleen cells of the group treated with DnaK-C3H mouse lymphomonocyte membrane peptide complexes are incapable of responding to stimulation with mitomycin-treated C3H cells. This is evidence of the induction of an allogenic tolerance.

The group treated with the peptide alone is also tolerated to a lesser extent.

The group treated with DnaK-beta-lactoglobulin peptide is not tolerant at all.

Moreover, the mixed cultures stimulated with another allogenic population, originating from a histoincompatible strain other than C3H, are all similar. This is evidence that no treatment has impaired or altered the MLC response capacity, and that the effect of the treatment is quite specific to the mouse strain from which the membrane peptides originate.

Figure 5:
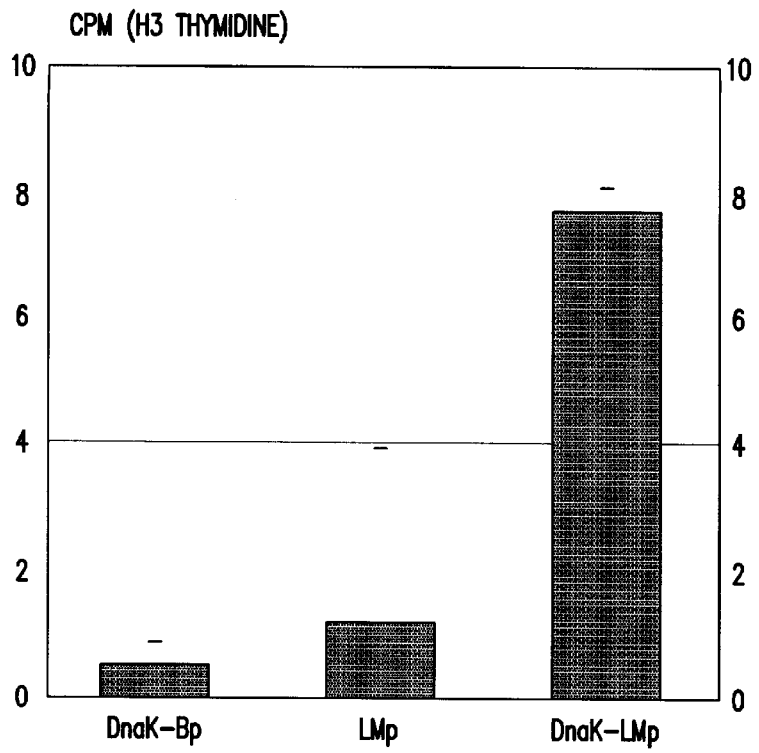
FIG. 5 depicts a mixed lymphocyte culture (MLC) response of cells from mice treated orally with DnaK-bp, LMp, and DnaK-LMp before grafting.

As represented in FIG. 5, the MLC response of cells from animals which are neither treated nor grafted is used to reveal the existence of foreign cells in a mixture of spleen cells from grafted animals, which would thus be of C3H origin in this case.

It appears that the spleens of mice treated orally before grafting with LMp and DnaK-LMp contain allogenic components since they give rise to a very significantly proliferative response which is different from the response of the control group treated with a DnaK-irrelevant peptide (beta-lactoglobulin) complex. The latter has a response which does not differ from the background noise.

Figure 6:
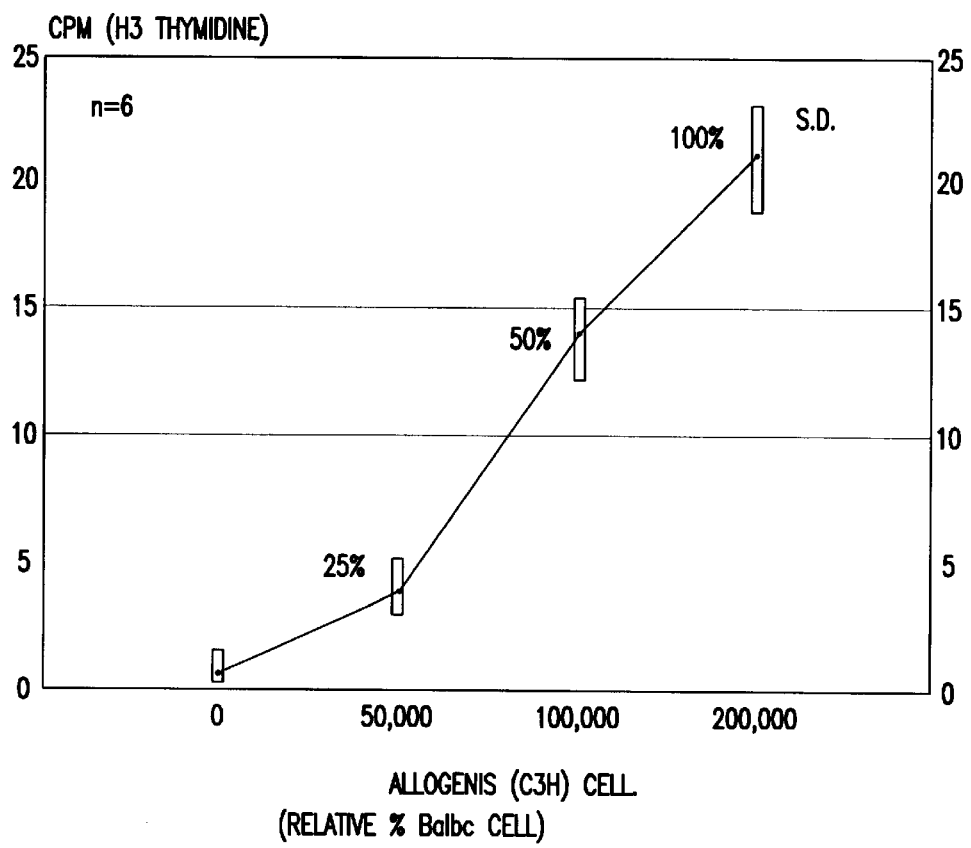
FIG. 6 depicts average MLC response levels of known C3H cell amount.

For comparative purposes, a series of mixed cultures were carried out in parallel with known and increasing amounts of C3H cells (FIG. 6). They give rise to a proliferative response which is proportional to the amount of foreign cells.

The average response level recorded with spleen cells from grafted animals and tolerized with DnaK-LMp complexes is thought to correspond to a content of about 30% of C3H cells.

The presence of cells of grafted type in the spleen is measured by immunofluorescence using an antibody which is specific for the MHC I of C3H (H-2kk) (Table 5). The group treated with DnaK-LMp contains 14.7% of this antibody on average, this value being significantly higher than that of the other two groups.

This presence of allo-antigens can only be observed providing that the grafted animal spleen cells are left to stand for at least one follows [sic] at 37° C. in the absence of serum, which suggests that it is essential to be able to re-express these antigens whose presence would thus be modified in vivo, quite probably by anti-H-2kk antibodies. This adds another mechanism of tolerance of the graft to the tolerance purely attributed to the responding T cells.

TABLE 1

Inhibitions of the M6 monoclonal antibody which binds nBLG by means of individual mouse sera: change as a function of time as a function of the type of complex administered orally.

| | | % of inhibition of the binding of M6 | | |
| --- | --- | --- | --- | --- |
| | | Average | Standard deviation | Number of cases |
| Group 1: Control (dBLG only) | | | | |
| SAMPLE | 1 | 45.0100 | 8.4146 | 8 |
| SAMPLE | 2 | 60.6750 | 3.9304 | 8 |
| SAMPLE | 3 | 59.6338 | 17.4714 | 8 |
| Group 2: dBLG-DnaK complexes | | | | |
| SAMPLE | 1 | 48.4350 | 7.0540 | 8 |
| SAMPLE | 2 | 56.3675 | 5.6146 | 8 |
| SAMPLE | 3 | 77.0975 | 3.8966 | 8 |

TABLE 1-continued

Inhibitions of the M6 monoclonal antibody which binds nBLG by means of individual mouse sera: change as a function of time as a function of the type of complex administered orally.

| | | % of inhibition of the binding of M6 | | |
|---|---|---|---|---|
| | | Average | Standard deviation | Number of cases |
| Group 3: dBLG- | | | | |
| SAMPLE | 1 | 23.7350 | 15.3990 | 8 |
| SAMPLE | 2 | 65.7013 | 6.2958 | 8 |
| SAMPLE | 3 | 65.3863 | 4.7270 | 8 |
| Group 4: dBLG- | | | | |
| SAMPLE | 1 | 24.9538 | 4.7972 | 8 |
| SAMPLE | 2 | 56.0100 | 4.3929 | 8 |
| SAMPLE | 3 | 80.0287 | 1.9401 | 8 |
| Group 5: dBLG- | | | | |
| SAMPLE | 1 | 37.3316 | 6.4248 | 8 |
| SAMPLE | 2 | 56.6962 | 5.5641 | 8 |
| SAMPLE | 3 | 87.1525 | 7.8731 | 8 |

TABLE 2

Inhibitions of the M7 monoclonal antibody which binds nBLG by means of individual mouse sera: change as a function of time as a function of the type of complex administered orally.

| | | % of inhibition of the binding of M7 | | |
|---|---|---|---|---|
| | | Average | Standard deviation | Number of cases |
| Group 1: Control (dBLG only) | | | | |
| SAMPLE | 1 | 70.0658 | 3.5541 | 8 |
| SAMPLE | 2 | 52.8224 | 2.3458 | 8 |
| SAMPLE | 3 | 57.0592 | 7.8996 | 8 |
| Group 2: dBLG-DnaK complexes | | | | |
| SAMPLE | 1 | 68.9145 | 2.6698 | 8 |
| SAMPLE | 2 | 51.6908 | 3.0857 | 8 |
| SAMPLE | 3 | 17.2697 | 8.0473 | 8 |
| Group 3: dBLG- | | | | |
| SAMPLE | 1 | 78.4276 | 3.4832 | 8 |
| SAMPLE | 2 | 50.8553 | 3.9778 | 8 |
| SAMPLE | 3 | 26.9145 | 3.2069 | 8 |
| Group 4: dBLG- | | | | |
| SAMPLE | 1 | 73.9671 | 3.1679 | 8 |
| SAMPLE | 2 | 28.5132 | 8.6072 | 8 |
| SAMPLE | 3 | 30.2829 | 14.2174 | 8 |
| Group 5: dBLG- | | | | |
| SAMPLE | 1 | 72.8355 | 4.7722 | 8 |
| SAMPLE | 2 | 22.2961 | 9.5040 | 8 |
| SAMPLE | 3 | 41.3684 | 6.4331 | 8 |

TABLE 3

Anti(native) nBLG antibody titers after logarithmic transformations: change as a function of time as a function of the type of complex administered orally.

| | | Ln of titers (A.U.) | | |
|---|---|---|---|---|
| | | Average | Standard deviation | Number of cases |
| Group 1: Control (dBLG only) | | | | |
| SAMPLE | 1 | 3.8526 | .4547 | 8 |
| SAMPLE | 2 | 4.2162 | .3395 | 8 |
| SAMPLE | 3 | 4.2059 | .2946 | 8 |
| Group 2: dBLG-DnaK complexes | | | | |
| SAMPLE | 1 | 3.9738 | .7957 | 8 |
| SAMPLE | 2 | 4.3749 | .6353 | 8 |
| SAMPLE | 3 | 3.2562 | .5057 | 8 |
| Group 3: dBLG- | | | | |
| SAMPLE | 1 | 3.7073 | .4435 | 7 |
| SAMPLE | 2 | 4.1348 | .5475 | 8 |
| SAMPLE | 3 | 4.3917 | .5047 | 8 |
| Group 4: dBLG- | | | | |
| SAMPLE | 1 | 4.3714 | .4215 | 8 |
| SAMPLE | 2 | 3.6419 | .4704 | 8 |
| SAMPLE | 3 | 3.9964 | .2724 | 8 |
| Group 5: dBLG- | | | | |
| SAMPLE | 1 | 4.1526 | .6401 | 8 |
| SAMPLE | 2 | 4.1739 | .4464 | 8 |
| SAMPLE | 3 | 3.6126 | .4873 | 8 |

TABLE 4

Differences in inhibition between the binding of the M6 and M7 antibodies to nBLG:

| | | % of inhibition of the binding of M6 - % of inhibition of the binding of M7 | | |
|---|---|---|---|---|
| | | Average | Standard deviation | Number of cases |
| Group 1: Control (dBLG only) | | | | |
| SAMPLE | 1 | −25.0558 | 9.0035 | 8 |
| SAMPLE | 2 | 7.8526 | 5.6470 | 8 |
| SAMPLE | 3 | 2.5745 | 19.8676 | 8 |
| Group 2: dBLG-DnaK complexes | | | | |
| SAMPLE | 1 | −20.4795 | 8.5253 | 8 |
| SAMPLE | 2 | 4.6767 | 6.1131 | 8 |
| SAMPLE | 3 | 59.8278 | 9.2686 | 8 |
| Group 3: dBLG- | | | | |
| SAMPLE | 1 | −54.6926 | 13.8705 | 8 |
| SAMPLE | 2 | 14.8460 | 6.4665 | 8 |
| SAMPLE | 3 | 38.4718 | 5.6903 | 8 |
| Group 4: dBLG- | | | | |
| SAMPLE | 1 | −49.0134 | 3.9824 | 8 |
| SAMPLE | 2 | 27.4968 | 10.6337 | 8 |
| SAMPLE | 3 | 49.7459 | 14.6732 | 8 |
| Group 5: dBLG- | | | | |
| SAMPLE | 1 | −35.5043 | 4.8959 | 8 |
| SAMPLE | 2 | 34.4002 | 13.4093 | 8 |
| SAMPLE | 3 | 45.7841 | 8.7931 | 8 |

TABLE 5

Persistant allogenic cells (H-2kk +) in the spleens of Balbc mice grafted with C3H cells:

Oral treatment

| DnaK-Bp | Lymphocyte membrane peptide (LMp) alone | DnaK-LMp |
|---|---|---|
| 1.0% | 0.9% | 14.2% |
| 1.5 | 2.8 | 25.0 |
| 0.5 | 3.6 | 9.2 |
| 0.5 | 3.7 | 10.4 |
| Average ET | Average ET | Average ET |
| 0.9%  0.5 | 2.7%  1.3 | 14.7%  7.2 |

Coupled T-tests:
 Dnak-LMp/DnaK-Bp: p=0.026
 DnaK-LMp/LMp: p=0.052

REFERENCES

1. Patterson, R. et al., *Allergy Proc.*, Vol. 15 (5), pp. 239–264 (1994)
2. Ferrick, D. A., Mak-TW *Tolerance and Self-Reactivity in V gamma* 1.1 *C gamma* 4 *transgenic mice*
3. Staines, U. et al., J. Rheumatol., Vol. 54 (3), pp. 145–154 (1995)
4. Polla, B. S. et al., *Clin. Exp. Allergy*, Vol. 23 (7), pp. 548–556 (1993)
5. Healy, A. M. et al., Ann. N. Y. Acad. Sci., Vol. 663, pp. 319–330 (1992)
6. Revillard, J. P. et al., *Dev. Biol. Stand.*, Vol. 77, pp. 31–37 (1992)
7. Bousquet, J. et al., *Allergy*, Vol. 49, pp. 31–36 (1994).

What is claimed is:

1. Pharmaceutical and/or food composition comprising: an adequate pharmaceutical and/or food vehicle, a stress protein selected from the group of the stress protein GroEL, GrpE, DnaK, and DNAJ, and at least one of the conformational or sequential epitopes of an antigenic structure which induces graft rejection, an allergic reaction, or an autoimmune reaction.

2. Pharmaceutical and/or food composition according to claim 1, characterized in that the pharmaceutical and/or food vehicle is adequate for mucosal or cutaneous administration.

3. Pharmaceutical and/or food composition according to claim 1, characterized in that the stress protein and the epitope form a complex.

4. Pharmaceutical and/or food composition according to claim 1, wherein the epitope is obtained by a hydrolysis of said antigenic structure.

5. Pharmaceutical and/or food composition according to claim 1 characterized in that the stress protein is a bacterial stress protein.

6. Pharmaceutical and/or food composition according to claim 5, characterized in that the bacterial stress protein is a stress protein from a saprophytic bacterium.

7. Pharmaceutical and/or food composition according to claim 5, characterized in that the stress protein is a stress protein from *E. coli*.

8. Pharmaceutical and/or food composition according to claim 1, wherein the antigenic structure is an allergen chosen from the group of the major allergic allergens present in milk, the major allergic antigens present in plants, animal hairs and animal venoms, the major antigens of the allergic reaction to acari, to the mite present in house dust (antigen P1 of *Dermatophogoides pteronyssinus*), the major antigen of *Aspergillus fumigatus*, staphylococcal enterotoxin B (SEB) and the major histocompatibility locus of type I or type II.

9. Pharmaceutical and/or food composition according to claim 1, comprising an immunosuppressant selected from the group of azathioprine, steroids, antilymphocyte globulins, cyclosporin A, rapamycin, KF506 (tacrolimus), lymphokines, analogs or agonists thereof, and a mixture thereof.

10. A method of preparing a medicine intended to modify a patient's immune response with respect to an antigenic structure which is specific to a pathology associated with graft rejection, an allergic reaction or an autoimmune reaction comprising the pharmaceutical and/ or food composition according to claim 1.

11. A method of preparing a medicine intended to desensitize atopic or non-atopic allergies comprising the pharmaceutical and/or food composition according to claim 1.

12. A method of preparing a medicine intended for the treatment or prevention of graft rejections comprising the pharmaceutical and/or food composition according to claim 1.

13. Pharmaceutical and/or food composition according to claim 4, wherein the epitope is obtained by an enzymatic hydrolysis of said antigenic structure.

14. Pharmaceutical and/or food composition according to claim 13, wherein the epitope is obtained by an enzymatic hydrolysis with pepsin of said antigenic structure.

15. Pharmaceutical and/or food composition according to claim 8, wherein the antigenic structure is further selected from the group consisting of bovine beta-lactoglobulin (BLG), pollens, and wasp venom.

16. A method of preparing a medicine intended for the treatment or prevention of autoimmune diseases comprising the pharmaceutical and/or food composition according to claim 1.

17. A method of preparing a medicine intended for the treatment or prevention of autoimmune diseases selected from the group of: infections associated with SLE (Systematic Lupus Erythematosus disease), Gougerot-Sjögren syndrome (or Sjögren's disease) and rheumatoid polyarthritis, sarcoidosis and osteopenia, spondylarthritis, scleroderma, multiple sclerosis, amyotrophic lateral sclerosis, hyperthyroidism, Addison's disease, autoimmune hemolytic anemia, Crohn's disease, Goddpasture's syndrome, Graves' disease, Hashimoto's thyroiditis, idiopathic purpural hemorrhage, insulin-dependent diabetes, myasthenia, pemphigus vulgaris, pernicious anemia, post-streptococcal glomerulonephritis, psoriasis, and spontaneous sterility comprising the pharmaceutical and/or food composition according to claim 1.

18. Pharmaceutical and/or food composition comprising: an adequate pharmaceutical and/or food vehicle, a stress protein selected from the group of the stress protein GroEL, GrpE, DnaK, and DNAJ, and at least one of the conformational or sequential epitopes of an antigenic structure, wherein the antigenic structure is selected from the group of major allergic allergens present in milk, the major allergic antigens present in plants, animal hairs and animal venoms, the major antigens of the allergic reaction to acari, to the mite present in house dust (antigen P1 of *Dermatophogoides pteronyssinus*), the major antigen of *Aspergillus fumigatus*, staphylococcal enterotoxin B (SEB) and the major histocompatibility locus of type I or type II.

19. Pharmaceutical and/or food composition according to claim 18, wherein the antigenic structure is further selected from the group of bovine beta-lactoglobulin (BLG), pollens, and wasp venom.

* * * * *